(12) United States Patent
Marin et al.

(10) Patent No.: US 11,409,131 B2
(45) Date of Patent: Aug. 9, 2022

(54) METHOD FOR DETERMINING THE CLYINDER OF AN OPHTHALMIC LENS

(71) Applicant: Essilor International, Charenton-le-Pont (FR)

(72) Inventors: Gildas Marin, Charenton-le-Pont (FR); Jean-Luc Perrin, Charenton-le-Pont (FR); Martha Hernandez-Castaneda, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 245 days.

(21) Appl. No.: 16/609,629

(22) PCT Filed: May 2, 2018

(86) PCT No.: PCT/EP2018/061207
§ 371 (c)(1),
(2) Date: Oct. 30, 2019

(87) PCT Pub. No.: WO2018/202713
PCT Pub. Date: Nov. 8, 2018

(65) Prior Publication Data
US 2020/0064656 A1    Feb. 27, 2020

(30) Foreign Application Priority Data

May 2, 2017   (EP) .................................. 17305485

(51) Int. Cl.
*G02C 7/02*    (2006.01)
*A61B 3/036*    (2006.01)

(52) U.S. Cl.
CPC .............. *G02C 7/027* (2013.01); *A61B 3/036* (2013.01)

(58) Field of Classification Search
CPC .......... G02C 7/027; G02C 7/02; G02C 7/024; G02C 7/028; A61B 3/036; A61B 3/1035; A61B 3/0025; A61B 3/0091; A61B 3/04
(Continued)

(56) References Cited

U.S. PATENT DOCUMENTS 4,105,303 A * 8/1978 Guyton ................. A61B 3/036
                                                          351/222
4,185,896 A * 1/1980 Buhler ................... A61B 3/036
                                                          351/234
(Continued)

FOREIGN PATENT DOCUMENTS

JP    2014-55793 A    3/2014

OTHER PUBLICATIONS

International Search Report and Written Opinion dated Jun. 29, 2018 in PCT/EP2018/061207 filed May 2, 2018.
(Continued)

*Primary Examiner* — Jordan M Schwartz
(74) *Attorney, Agent, or Firm* — Oblon, McClelland, Maier & Neustadt, L.L.P.

(57) ABSTRACT

A method for determining a cylinder of an ophthalmic lens to be mounted on a spectacle frame is provided, the method including: providing a measuring device configured to run a Jackson Cross Cylinder procedure; determining components of a first vector of the cylinder in a two-dimensional vector cylinder representation; and determining components of a second vector of the cylinder in the two-dimensional vector cylinder representation, the components of the second vector of the cylinder being determined such that a Euclidian distance between the first vector and the second vector is independent of a value of the cylinder.

14 Claims, 3 Drawing Sheets

(58) Field of Classification Search
USPC .................. 351/241, 159.07, 159.22, 159.74
See application file for complete search history.

(56) References Cited

U.S. PATENT DOCUMENTS

| | | | | |
|---|---|---|---|---|
| 6,467,906 | B1* | 10/2002 | Alpins | ................. A61B 3/0025 351/212 |
| 2003/0030774 | A1 | 2/2003 | Raasch | |
| 2006/0139573 | A1* | 6/2006 | Sakurada | ............... A61B 3/036 351/211 |
| 2013/0107204 | A1* | 5/2013 | Spratt | .................... G02C 7/061 351/159.74 |
| 2015/0346512 | A1 | 12/2015 | Spratt et al. | |
| 2016/0327808 | A1* | 11/2016 | Hatanaka | ............... G02C 7/066 |
| 2019/0313904 | A1* | 10/2019 | Dave | ................... A61B 3/0285 |

OTHER PUBLICATIONS

Revert, A. M. et al., "An alternative clinical routine for subjective refraction based on power vectors with trial frames," Ophthalmic & Physiological Optics, vol. 37, No. 1, 2017, pp. 24-32, XP055423924.
Furlan, W. D. et al., "Jackson cross cylinder—simple formulation of its optical principles," Optica Applicata, vol. 30, No. 2-3, 2000, pp. 421-429, XP055423917.

* cited by examiner

METHOD FOR DETERMINING THE CLYINDER OF AN OPHTHALMIC LENS

FIELD OF THE INVENTION

The invention relates to a method for determining astigmatism of an eye of a person, a device for determining at least the cylindrical parameter of an ophthalmic lens to be mounted on a spectacle frame and a method for ordering a new optical equipment for a person.

BACKGROUND OF THE INVENTION

Usually, a person wishing to have an optical equipment goes to see an eye care practitioner.

The usual methods for determining the dioptric parameters of an ophthalmic lens to be provided to a person have a number of drawbacks among which the difficulty to determine the astigmatism of the eye of a person.

Furthermore, the usual methods are usually distressing for the person and therefore are usually not carried out over a long period of time. Thus, the eye care practitioner may need to shorten the test because the person under test is starting to be impatient and/or may be under stress and experience eye fatigue and/or has a lack of attention.

The Jackson Cross Cylinder method is currently the most precise method to determine astigmatism but this process is not easy to handle, both for the eye care practitioner and the person.

Typically, the person is required to compare two positions of a test lens and very often does not easily know which one to choose. The procedure may not be well adapted to the sensitivity of the patient.

The person sometimes does not understand correctly the instructions given by the eye care practitioner when positions of the test lenses change, or the eye care practitioner changes the position at a speed not suitable for the person, for example too quickly or not quick enough, or the person forgets the quality the image showed previously. These types of troubles can lead to wrong answers and the prescription could be not accurate and precise enough to find the exact astigmatism of the person.

The classical refraction process using cross cylinders demands a large experience and competencies from eye care practitioner for an accurate result. Result is thus highly dependent of the eye care practitioner. Furthermore, the classical refraction process may not be carried out by a non-experienced person or by the person itself needing a prescription.

Especially in case of low astigmatism, it is also difficult to tiny refine the axis. The steps in degree must be adapted according to the power level of astigmatism of the person. If initial astigmatism is null or almost null, a specific procedure has to be used, the classic cross cylinders procedure being no more relevant.

Finally, there is a lack of accuracy in the axis also because the referential are not well defined and usually not the same at the time of refraction and at the time of mounting the lenses in the frame and thus when worn at the end.

Therefore, there is a need for a method for determining the astigmatism of an eye of a person that would not present the above-mentioned drawbacks.

One object of the present invention is to provide such method.

SUMMARY OF THE INVENTION

To this end, the invention proposes a method for determining astigmatism of an eye of a person, the method comprising a measuring device providing step during which a measuring device adapted to run a Jackson cross cylinder procedure is provided, a first vector determining step, during which the components of a first vector of the cylinder in a two-dimensional vector cylinder representation are determined, a second vector determining step, during which the components of a second vector of the cylinder in the two-dimensional vector cylinder representation are determined wherein the second vector components being determined such that the Euclidian distance between first and second vector is independent of the value of the cylinder.

Advantageously, the method of the invention allows determining the astigmatism of an eye of a person avoiding the size of the cylinder issues. In other words, the method of the invention and the accuracy of the method of the invention are independent of the value of the astigmatism of the person.

Furthermore, in the method of the invention, the first and second vector are processed in the same way providing a more homogenous and accurate result.

Another object of the invention is a method for determining the cylinder of an ophthalmic lens to be mounted on a spectacle frame, the method comprising a measuring device providing step during which a measuring device adapted to run a Jackson cross cylinder procedure is provided, a first vector determining step, during which the components of a first vector of the cylinder in a two-dimensional vector cylinder representation are determined, a second vector determining step, during which the components of a second vector of the cylinder in the two-dimensional vector cylinder representation are determined wherein the second vector components being determined such that the Euclidian distance between first and second vector is independent of the value of the cylinder.

Advantageously, the method of the invention allows determining the cylinder of an ophthalmic lens avoiding the size of the cylinder issues.

The method for determining the astigmatism of an eye of a person and the method for determining the cylinder of an ophthalmic lens to be mounted on a spectacle frame may comprise one or more additional features according to further embodiments which can be considered alone or in combination:

the ophthalmic lens is adapted to correct astigmatism of an eye of a person;

the second vector components are determined such that the distance between first and second vector is independent of the value of the cylinder when the vector components are expressed in a J0/J45 coordinate system; and/or the method further comprises:
a target zone determining step, during which a target zone in the two-dimensional vector cylinder representation is determined, the target zone corresponding to part of the two-dimensional vector cylinder representation in which the components of a second vector of the cylinder are to be tested,
the size of the target zone determined during the zone determining step is independent of the value of the cylinder; and/or the method further comprises expressing the sphere and cylinder correction as vectors in a third-dimensional vector representation; and/or the size of the target zone is adapted to the sensitivity of the person to blur; and/or the value of the Jackson Cross Cylinder is adapted to the sensitivity of the person to blur; and/or the value of the Jackson Cross Cylinder is based on the target zone size; and/or the size of the target zone is modified during the procedure; and/or the value of the Jackson Cross Cylinder is modified during the procedure; and/or the vector decomposition of the cylinder is done according to two orthogonal directions; and/or one of the two orthogonal directions correspond to the initial astigmatism direction of the eye of the person; and/or the two orthogonal directions are chosen at +22.5° and −22.5° from the initial astigmatism direction of the eye of the person; and/or during the Jackson cross cylinder procedure the components of the second vector are determined by first selecting a unique direction of variation by testing values on the periphery of the target zone only; and/or during the Jackson cross cylinder procedure the components of the second vector are determined by further selecting a unique direction of variation in the third-dimension by testing values on the periphery of the target zone only, the selection being separated in two steps: first selecting a unique direction of variation by testing values on the periphery of the target zone projected in the two-dimension cylinder plan, second, selecting a final unique direction of variation by testing values on the periphery of the target zone projected in the two-dimension plan including the first selected direction and perpendicular to the cylinder plan; and/or during the Jackson cross cylinder procedure the components of the second vector are determined by testing diametrically opposed values on the periphery of the target zone; and/or the target zone has a circular shape.

The invention further relates to a method for determining astigmatism of both eyes of a person, wherein the astigmatism of both eyes of the person is determined using a method according to the invention with the same variation of cylinder components during the Jackson cross cylinder for both eyes.

According to further embodiments which can be considered alone or in combination:

the target zone for the second eye may be based on the value determined for both the first eyes; and/or the dominant eye of the person may be tested second; and/or the target zone for the second eye is based on the value determined for the first eye.

The invention further relates to a device for determining at least the cylindrical parameter of an ophthalmic lens to be mounted on a spectacle frame, the device comprising:

a visual target, a adjustable cylinder lens through which the person sees the visual target, and a control panel allowing to control the adjustable cylinder so as to carry out the method according to the invention.

The invention also relates to a method for ordering a new optical equipment for a person, the method comprising:

determining the astigmatism of the person using a method according to the invention, an ordering step during which an order request for a new optical equipment is sent to a distant entity, the order request comprising at least an indication of the astigmatism of the person and new optical equipment identification data.

The invention also relates to a method for ordering a new optical equipment for a person, the method comprising:

determining the cylinder of an ophthalmic lens to be mounted on a spectacle frame using a method according to the invention, an ordering step during which an order request for a new optical equipment is sent to a distant entity, the order request comprising at least an indication of the cylinder of an ophthalmic lens to be mounted on a spectacle frame and new optical equipment identification data.

The invention further relates to a method for providing optical equipment for a person, the method comprising:

an order receiving step during which an order request generated by a method according to the invention, a parameter determining step during which at least one optical parameter of the optical equipment is determined based on the at least one received order request, an optical equipment providing step during which a new optical equipment is provided to the person based on the astigmatism, or on the cylinder of an ophthalmic lens to be mounted on a spectacle frame, determined using a method according to the invention.

The invention further relates to a computer program product comprising one or more stored sequences of instructions that are accessible to a processor and which, when executed by the processor, causes the processor to carry out at least the first and second vector determining steps of the method according to the invention.

The invention also relates to a computer-readable storage medium having a program recorded thereon; where the program makes the computer execute at least the first and second vector determining steps of the method of the invention.

The invention further relates to a device comprising a processor adapted to store one or more sequence of instructions and to carry out at least the first and second vector determining steps of the method according to the invention.

BRIEF DESCRIPTION OF THE DRAWINGS

Embodiments of the invention will now be described, by way of example only, and with reference to the following drawings in which.

DETAILED DESCRIPTION OF PREFERRED EMBODIMENTS

Elements in the figures are illustrated for simplicity and clarity and have not necessarily been drawn to scale. For example, the dimensions of some of the elements in the figure may be exaggerated relative to other elements to help improve the understanding of the embodiments of the present invention.

The invention relates to a method for determining astigmatism of an eye of a person or for determining the cylinder of an ophthalmic lens to be mounted on a spectacle frame. In embodiments, the ophthalmic lens is adapted to correct astigmatism of an eye of a person.

The method of the invention uses a vector decomposition of the cylinder, rather than the standard polar form power or magnitude and axis or orientation decomposition, during a Jackson cross cylinder procedure to evaluate accurately the astigmatism of the eye of a person or to evaluate accurately the cylinder of an ophthalmic lens to be mounted on a spectacle frame.

Figure 1:
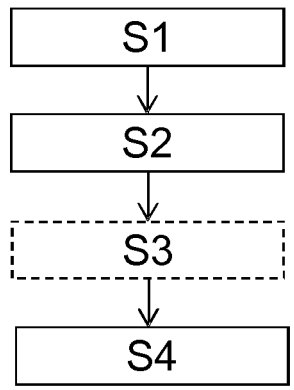
FIG. 1 is a flow chart representing a method for determining astigmatism of an eye of a person, or the cylinder of an ophthalmic lens to be mounted on a spectacle frame, according to the invention.

As illustrated in FIG. 1, the method according to the invention comprises at least:
  a measuring device providing step S1,
  a first vector determining step S2, and
  a second vector determining step S4.

During the measuring device providing step S1, a measuring device adapted to run a Jackson cross cylinder procedure is provided.

During the first vector determining step S2, the components of a first vector of the cylinder in a two-dimensional vector cylinder representation are determined. During the second vector determining step S4, the components of a second vector of the cylinder in the two-dimensional vector cylinder representation are determined.

According to the invention the second vector components are determined during the second vector determining step S4 in such a way that the Euclidian distance between first and second vectors is independent of the value of the cylinder.

Preferably, the vector decomposition of the cylinder is done according to two orthogonal directions.

Figure 3A:
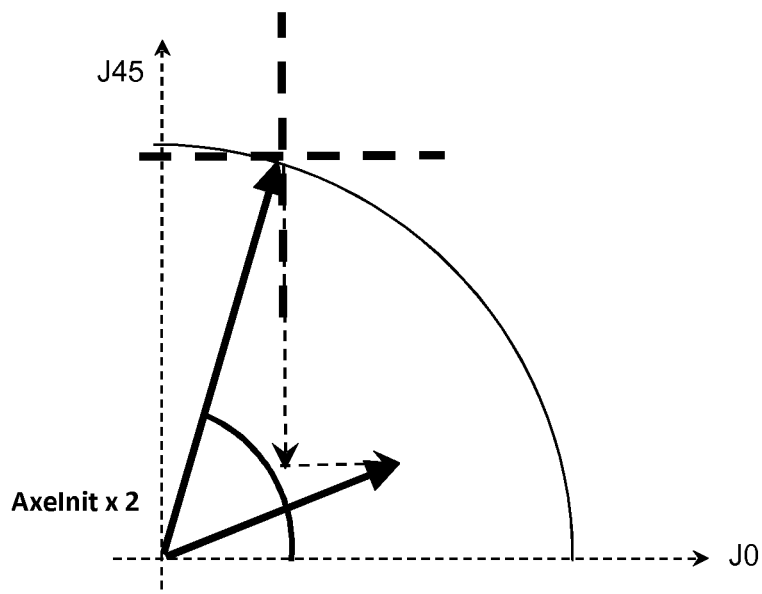

For example, the method of two orthogonal directions may be a J0/J45 decomposition as illustrated on FIG. 3a. The J0/J45 decomposition corresponds to the replacement of the classical sphero-cylindrical notation by a 3-tuple of orthogonal values (S, J0, J45) defined as a spherical lens of power S and two Jackson crossed cylinder lenses one at axis 0° with a power $J0=(-C/2)*\cos(2*axis)$ and the other at axis 45° with a power $J45=(-C/2)*\sin(2*axis)$, as the astigmatism decomposition of the polar form of astigmatism (C, axis).

Figure 3B:
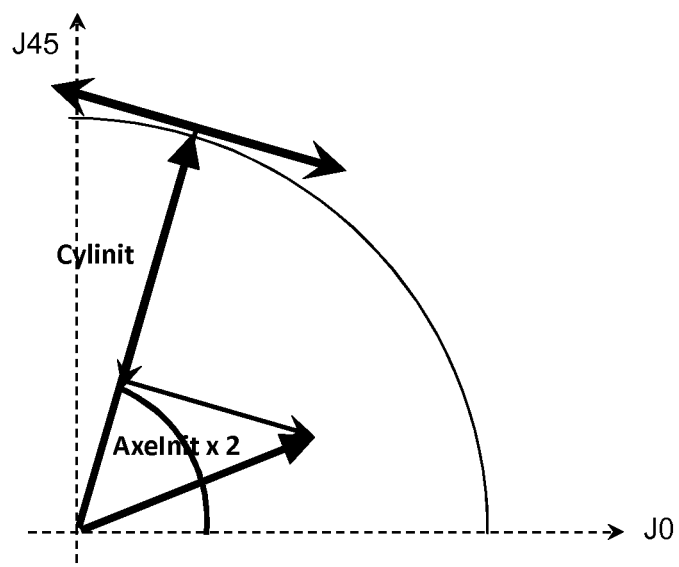

To be closer to the standard Jackson crossed cylinder procedure, the two-orthogonal direction may correspond to the initial astigmatism direction and its perpendicular direction as illustrated on FIG. 3b.

Figure 3C:
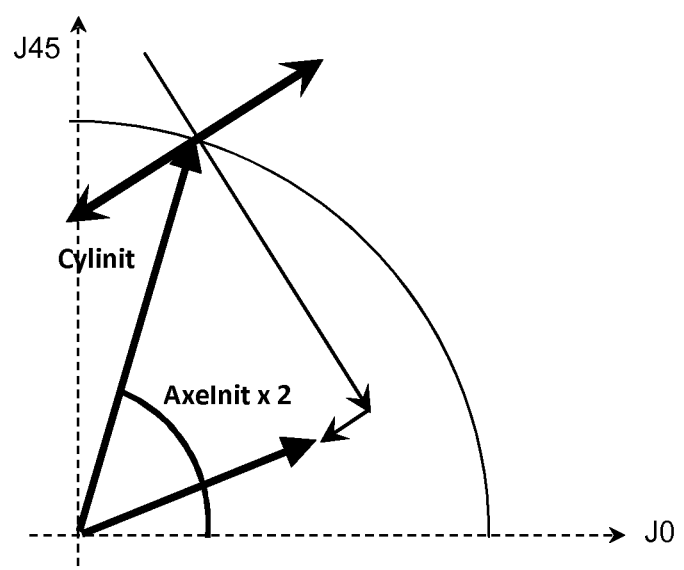

Alternatively, as illustrated on FIG. 3c, the two-orthogonal direction may be a decomposition at +22.5° and −22.5° from the initial astigmatism direction to uniform the perception along the two directions. When the initial astigmatism is null, one may set the initial direction to zero by convention.

Advantageously, the method of the invention provides the same accuracy independently of the value of the cylinder being tested. Any change or step defined during the Jackson crossed cylinder procedure is defined in Diopters along one of the orthogonal direction. The new value to apply may then be converted into (Cyl, axis) if needed.

For example, one may come back to the standard polar form of astigmatism (Cyl, axis), in the J0/J45 coordinate system, using the following formulae:

$Cyl=2*\sqrt{(J0^2+J45^2)}$ and $axis=a\tan(-J45/J0)/2+Jdir$, with Jdir the deviation between the first direction and the initial astigmatism direction.

Advantageously, the measuring device provided during the measuring device providing step comprises a phoropter or any corrective system allowing to apply continuous values. The tested values may be rounded at any time during the process to be applied on a corrective system allowing only discrete values, for example trial frames or standard phoropter using lenses at 0.25 D steps every 1° steps axis.

The method of the invention allows processing both directions in the same way, providing more homogeneous determination.

According to an aspect of the invention it may be recommended to start the method of the invention with the direction that is closer to the initial cylindrical correction direction. Typically, one may start with the cylinder power instead of axis as usual when implementing the Jackson crossed cylinder procedure.

The reason for that is that the power direction is easier for the person under test to handle since the perception aspect is changing by reducing or increasing the blur in similar aspect if respectively decreasing or increasing the distance to the preferred correction. On the contrary changing the axis result in a more complex perceptual change making the choice for the person under test more difficult and therefore the overall result less accurate.

When starting the method of the invention to determine the best correction, for the first direction, the person under test has to deal with the remaining residual error of the correction on the $2^{nd}$ direction whereas for the $2^{nd}$ direction axis, the residual error on the $1^{st}$ direction has already been minimized. Thus, it is easier to handle the more complex correction i.e. the axis direction when the residual error is minimized on the other direction.

Moreover, the starting point is usually more precise on the axis than for the power of astigmatism, thus again, making it easier to handle first the power keeping with the smallest residual error on the other axis. It is also better to start minimizing the largest residual error.

Each component may be tested separately with a simple staircase procedure.

Alternatively, the method may be implemented using a direct 2D method moving freely in the J0/J45 plan, for example with a mouse, or use a predetermined or randomized set of 2D points.

The measurements may be repeated to estimate the best position by determining the parameters of the best elliptic standard deviation calculated from the repeated results.

The direction in which the method is to be carried out may be deducted from the answers of the person under test as follows:
  If lens 1 is preferred, increase the tested component.
  If lens 2 is preferred, decrease the tested component.
  If don't know answer, go on in the same direction as previously.

The method of the invention can be stopped at a fixed amount of repetitions, a fixed amount of reversals, or after several "I don't know" answers.

According to an embodiment of the invention, the answers of the person under test may be registered directly with a keypad or other allowing 3 types of answer: lens 1, lens 2, "don't know or same".

An additive process is needed to allow going from lens 1 to lens 2. Any of the previous key or combination may be used. The "don't know" key has been tested and seems an easy and comprehensive solution.

An alternative solution may be to have the person under test go from lens 1 to lens 2 alternatively and stop on the preferred lens, i.e. one answer or chose "don't know".

The "don't know" answer may be considered as the same answer as the previous answer before any processing.

If first answer is "don't know", a modification of the initial value may be requested.

A sound may be played as a feedback for the person under test that the answer has been taken into account.

Alternatively, a visual feedback may be displayed, for example highlighting a sign on the answered side.

Figure 4:
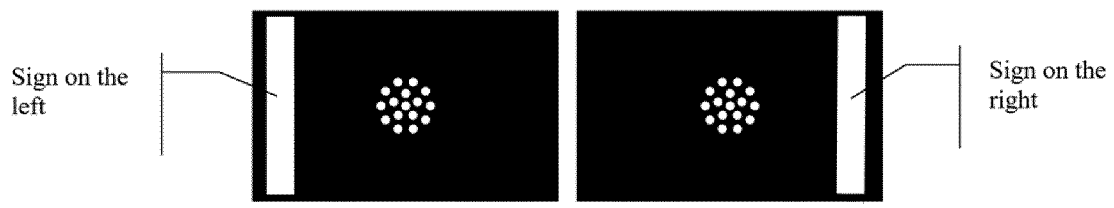
FIG. 4 illustrates an example of stimulus that may be used when implementing the method of the invention.
Figure 2:
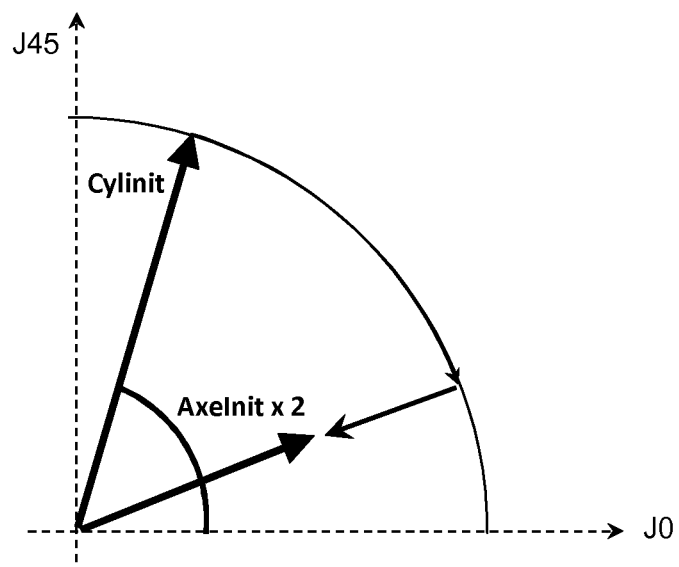
FIG. 2 illustrates a classic approach for determining the cylinder component of the astigmatism of the eye of a person cylinder of an ophthalmic lens to be mounted on a spectacle frame FIG. 3 illustrate different embodiment for determining the cylinder component of the astigmatism of the eye of a person, or the cylinder of an ophthalmic lens to be mounted on a spectacle frame.

The display or sound feedback should indicate to the person under test whether currently lens 1 or lens 2 is used, for example display a sign/bar on left or right corresponding to the side to answer if chosen as illustrated on FIG. 4.

The displayed stimulus may be the Maltese points classically used for a Jackson cross cylinder procedure. Any other optotypes or stimulus may be used.

Inverse contrast, i.e. white optotype on black background appear to provide better results, however standard contrast may also be used. Acuity charts (ETDRS . . . ) can also be used in order to measure the acuity of the person under test for example to adapt the Jackson cross cylinder value along the refraction.

As illustrated on FIG. 1, the method according to the invention may further comprise, for example prior to the second vector determining step, a target zone determining step S3.

During target zone determining step S3 a target zone in the two-dimensional vector cylinder representation is determined. The target zone corresponding to part of the two-dimensional vector cylinder representation in which the components of a second vector of the cylinder are to be tested.

The size of the target zone determined during the zone determining step is independent of the value of the cylinder.

The size of the target zone and/or the value of the Jackson Cross Cylinder may be adapted to the sensitivity of the person under test to blur. The sensitivity of the person under test to blur may be evaluated prior to the method of the invention or when carrying out the method of the invention.

The target zone may have a circular shape.

The value of the Jackson Cross Cylinder used when carrying out the method of the invention may be based on the target zone size determined during the target zone determining step S3.

To increase accuracy of the method of the invention, the size of the target zone and/or the value of the Jackson Cross Cylinder may be modified during the Jackson cross cylinder procedure.

Having determined a target zone allows having during the Jackson cross cylinder procedure the components of the second vector determined by first selecting a unique direction of variation by testing values on the periphery of the target zone only.

According to an embodiment of the invention, during the Jackson cross cylinder procedure the components of the second vector are determined by further selecting a unique direction of variation in the third-dimension by testing values on the periphery of the target zone only.

The selection being separated in two steps: first selecting a unique direction of variation by testing values on the periphery of the target zone projected in the two-dimension cylinder plan, second, selecting a final unique direction of variation by testing values on the periphery of the target zone projected in the two-dimension plan including the first selected direction and perpendicular to the cylinder plan.

According to an embodiment of the invention, during the Jackson cross cylinder procedure the components of the second vector may be determined by testing diametrically opposed values on the periphery of the target zone.

In the sense of the invention "Testing" a new cylindrical correction value included in the target zone is equivalent to presenting to the person under test 2 corrections to be compared which do not necessary correspond to possible final corrections and are not required to be included in the target zone. Indeed, the 2 corrections to be compared usually correspond to the new cylindrical correction value under test more or less a certain amount of cylinder with null spherical component, named the Jackson Cross Cylinder.

To accurately apply the determined correction to the person under test it may be required to define a proper referential coordinate system to ensure the correction found is the same as the one provided and worn by the person. It is preferable to define a common referential for the axis origin at the time of refraction and mounting to ensure a proper orientation of cylinder correction in the frames.

For that, one may use a referential axis that goes through the 2 pupils of the person under test.

Thus, when carrying out the method of the invention, the phoropter or corrective system is aligned on the 2 pupil axis of the person under test instead of habitually horizontally set. This axis may be used as the null reference for cylinder axis orientation.

The same reference can be used when mounting the lenses in the frame since optician usually gets the pupil height in the frame to align the optical center of the lenses.

By using this reference, we can ensure the accuracy of the full astigmatism correction.

Any other reference attached to the person may be relevant. For example, we may use the commissure of the eyes or the ears position.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method for determining a cylinder of an ophthalmic lens to be mounted on a spectacle frame, the method comprising
    providing a measuring device configured to run a Jackson Cross Cylinder procedure;
    determining components of a first vector of the cylinder in a two-dimensional vector cylinder representation;
    determining components of a second vector of the cylinder in the two-dimensional vector cylinder representation; and
    determining a target zone in the two-dimensional vector cylinder representation, performing a series of tests to determine components of the second vector value within the target zone, the target zone corresponding to part of the two-dimensional vector cylinder representation in which the components of the second vector of the cylinder are to be tested, wherein the components of the second vector of the cylinder are determined such that a Euclidian distance between the first vector and the second vector is independent of a value of the cylinder, and wherein a size of the determined target zone is independent of the value of the cylinder.

2. The method according to claim 1, wherein the components of the second vector of the cylinder are expressed in a J0/J45 coordinate system, and wherein the components of the second vector of the cylinder are determined such that the Euclidian distance between the first vector and the second vector is independent of the value of the cylinder.

3. The method according to claim 1, further comprising expressing a sphere and cylinder correction as vectors in a third-dimensional vector representation.

4. The method according to claim 1, wherein the size of the determined target zone and/or a value of the Jackson Cross Cylinder is adapted to a sensitivity of a person to blur.

5. The method according to claim 3, wherein a value of the Jackson Cross Cylinder is based on the size of the determined target zone.

6. The method according to claim 1, wherein the size of the determined target zone and/or a value of the Jackson Cross Cylinder is modified during running of the Jackson Cross Cylinder procedure.

7. The method according to claim 1, further comprising performing a vector decomposition of the cylinder, wherein a vector decomposition of the cylinder is according to two orthogonal directions.

8. The method according to claim 7, wherein the ophthalmic lens is configured to correct astigmatism of an eye of a person, and one direction of the two orthogonal directions corresponds to an initial astigmatism direction of the eye of the person.

9. The method according to claim 1, wherein during running of the Jackson Cross Cylinder procedure the components of the second vector of the cylinder are determined by first selecting a unique direction of variation by testing values on a periphery of the target zone only.

10. The method according to claim 9, further comprising expressing a sphere and cylinder correction as vectors in a third-dimensional vector representation, wherein during the running of the Jackson Cross Cylinder procedure the components of the second vector of the cylinder are determined by further selecting a second unique direction of variation in a third-dimension by testing values on the periphery of the target zone only, the selecting of the second unique direction being separated in two steps:

first, selecting the second unique direction of variation by testing values on the periphery of the target zone projected in the two-dimension cylinder plan, and second, selecting a final second unique direction of variation by testing values on the periphery of the target zone projected in the two-dimension plan including the first selected direction and perpendicular to the two-dimension cylinder plan.

11. The method according to claim 1, wherein the determined target zone has a circular shape.

12. A device for determining at least a cylindrical parameter of an ophthalmic lens to be mounted on a spectacle frame, the device comprising:

a visual target;

an adjustable cylinder lens through which a person sees the visual target; and a control panel configured to allow control of the adjustable cylinder so as to carry out the method according to claim 1.

13. A method for ordering a new optical equipment for a person, the method comprising:

determining a cylinder of an ophthalmic lens to be mounted on a spectacle frame by the method according to claim 1; and an ordering step during which an order request for the new optical equipment is sent to a distant entity, the order request comprising at least an indication of the cylinder of the ophthalmic lens and identification data of the new optical equipment identification.

14. A method for providing new optical equipment for a person, the method comprising:

ordering a new optical equipment for a person, comprising determining a cylinder of an ophthalmic lens to be mounted on a spectacle frame by the method according to claim 1, and an ordering step during which an order request for the new optical equipment is sent to a distant entity, the order request comprising at least an indication of the cylinder of the ophthalmic lens and identification data of the new optical equipment identification;

an order receiving step during which an order request generated by the ordering step is received;

a parameter determining step during which at least one optical parameter of the optical equipment is determined based on the at least one received order request; and an optical equipment providing step during which the new optical equipment is provided to the person based on the determined cylinder of the ophthalmic lens to be mounted on the spectacle frame.

\* \* \* \* \*

UNITED STATES PATENT AND TRADEMARK OFFICE
CERTIFICATE OF CORRECTION

| | |
|---|---|
| PATENT NO. | : 11,409,131 B2 |
| APPLICATION NO. | : 16/609629 |
| DATED | : August 9, 2022 |
| INVENTOR(S) | : Gildas Marin et al. |

It is certified that error appears in the above-identified patent and that said Letters Patent is hereby corrected as shown below:

On the Title Page

Item (54) and in the Specification Column 1, Line 1, the Title of the Invention is misspelled.
Should read:
--METHOD FOR DETERMINING THE CYLINDER OF AN OPHTHALMIC LENS--

Signed and Sealed this
Fifteenth Day of November, 2022

*Katherine Kelly Vidal*

Katherine Kelly Vidal
*Director of the United States Patent and Trademark Office*